United States Patent [19]

Borovsky et al.

[11] Patent Number: 5,130,253
[45] Date of Patent: Jul. 14, 1992

[54] DNAS ENCODING MOSQUITO OOSTATIC HORMONES

[75] Inventors: Dov Borovsky, Vero Beach; David A. Carlson, Gainesville, both of Fla.

[73] Assignees: University of Florida, Gainesville, Fla.; The United States of America as represented by the Department of Agriculture, Washington, D.C.

[21] Appl. No.: 645,087

[22] Filed: Jan. 22, 1991

Related U.S. Application Data

[62] Division of Ser. No. 335,169, Apr. 7, 1989, Pat. No. 5,011,909.

[51] Int. Cl.$^5$ .................... C12N 15/63; C12V 15/16
[52] U.S. Cl. .................... 435/320.1; 536/27
[58] Field of Search .................... 536/27; 435/320.1

[56] References Cited

PUBLICATIONS

Borovsky, *Archives of Insect Biochemistry and Physiology*, 2:333–349 (1985).

Primary Examiner—Richard A. Schwartz
Assistant Examiner—S. L. Nolan
Attorney, Agent, or Firm—Saliwanchik & Saliwanchik

[57] ABSTRACT

The subject invention concerns three novel peptides which have the property of interfering with the biosynthesis of the enzyme trypsin in an insect gut. This property enables the use of these peptides to inhibit the formation of progeny in blood-ingesting insects, since trypsin is an essential enzyme for food digestion which provides the essential building blocks for egg development in such insects.

8 Claims, No Drawings

DNAS ENCODING MOSQUITO OOSTATIC HORMONES

This is a division of application Ser. No. 07/335,169, filed Apr. 7, 1989, now U.S. Pat. No. 5,011,909.

BACKGROUND OF THE INVENTION

The existence of antigonadotropins or hormones that inhibit egg development, oostatic hormones, has been demonstrated in the cockroach, eye gnat, crustaceans, house fly, and mosquitoes (Borovsky, D. [1985], Arch. Insect Biochem. Physiol. 2:333-349). To our knowledge no substance has been purified to homogeneity, identified and synthesized and shown to have a dose response effect inhibiting egg development and proteolytic enzyme biosynthesis against flies, sand flies, Culicoides, cat fleas and different species of mosquitoes.

Borovsky, D. (1985), Arch. Ins. Biochem. Physiol. 2:333-349 has purified the hormone 7,000-fold and disclosed that injection of a hormone preparation into the body cavity of blood imbibed insects caused inhibition of egg development and sterility in insects. Following these observations Borovsky, D. (1988), Arch. Ins. Biochem. Physiol. 7:187-210 disclosed that injection or passage of a peptide hormone preparation into blood sucking insects caused inhibition in the biosynthesis of serine esterase, trypsinlike and chymotrypsinlike enzymes biosynthesis in the epithelium cells of the gut. Since trypsin is the major proteolytic enzyme synthesized in this insect (about 70-80%), the blood meal is not digested efficiently, and consequently free amino acids needed for the synthesis of the yolk protein synthesis in the fat body are not released into the hemolymph, yolk protein is not synthesized and yolk is not deposited in the ovaries, and egg development is arrested.

The rapid increase in pesticide resistance of disease-borne arthropods makes our hormonal approach a safer alternative to the chemical approach (e.g., synthetic pyrethroid, organochlorine, and organophosphates).

BRIEF SUMMARY OF THE INVENTION

The subject invention concerns novel peptide hormones that inhibit digestion in blood-ingesting insects, thus causing sterility (inhibition of egg development) in the treated insects. The subject invention specifically concerns three novel peptides having the formulas:

$$H_2NYDPAP_6COOH \quad (1)$$

$$H_2NDYPAP_6COOH \quad (2)$$

$$H_2NPAP_6COOH \quad (3)$$

All three compounds show potent biological activity against *Aedes aegypti, Culex quinquefasciatus, Anopheles albimanus, Anopheles quadrimaculatus, Lutzomyia anthophora, Culicoides variipennis, Stomoxys calcitrans, Musca domestica* and *Ctenocephalides felis*. The compounds are white powders that are highly soluble in water. They can be synthesized on a commercial peptide synthesizer.

Also included in this invention are addition salts, complexes, or prodrugs such as esters of the compounds of this invention, especially the nontoxic pharmaceutically or agriculturally acceptable acid addition salts.

The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The formulas have two weak acidic groups (carboxyl groups) on the aspartic acid (D) and on the proline (P) at the caroxyl end. Thus, esterification at these groups to form derivatives such as the methyl or ethyl esters, can be prepared by standard procedures. Derivation of these compounds with long chain hydrocarbons will facilitate passage through the cuticle into the body cavity, and could be used as a commercial product to sterilize blood sucking adult insects and inhibit digestion of food in larvae. For example, the compounds of the invention can be topically applied onto insect adults. Treatment by injection of the compounds of the invention into adult female mosquitos after a blood meal stops egg development, thus rendering the female mosquito sterile and unable to reproduce. Also, using known techniques of molecular biology, it may possible to feed mosquito larvae genetically engineered bacteria producing oostatic hormone and infect other insect larvae with bacteria or a baculovirus containing the oostatic gene, making them unable to digest their food and subsequently starve them to death. The production of the claimed peptide compounds by bacteria would be responsible for the starvation activity in larvae and sterilization in adults. This type of treatment of blood-ingesting insect larvae is analogous to the use of bacteria to control insect populations. For example, *Bacillus thuringiensis* var. *israelensis* controls a wide variety of disease-bearing insects, commercially important insects and pest insects. This bacterium synthesizes crystals of protein that are toxic to insects (usually larvae) that ingest them. Such products are in wide use worldwide. They are often applied to large fields or to entire river systems and also have been molecularly engineered into plants.

The peptides of the invention are particularly active against blood-sucking insects, particularly against species of mosquitoes such as *Aedes aegypti* that are potential vectors of arthropod-borne viral diseases (arboviruses). These insect species utilize serine esterases (trypsin and chymotrypsinlike enzymes) as their primary blood digesting enzymes. The inhibition of proteolytic enzyme biosynthesis and egg development in several insect species is demonstrated in Table 1.

TABLE 1

| Effect of Oostatic Hormone on Egg Development and Trypsinlike Enzymes Biosynthesis in Several Species of Insects. | | | |
|---|---|---|---|
| Insect Species | Oostatic hormone (nmol) | Inhibition of ovarian development (%) | Inhibition of trypsin synthesis (%) |
| Mosquito: | | | |
| *Aedes aegypti* | 2.86 | 98 | 86 |
| *Culex quinquefasciatus* | 3.6 | 91 | N.D. |
| *Anopheles albimanus* | 1.83 | 100 | N.D. |
| Sand fly: | 0.477 | 50 | 30 |
| *Lutzomyia anthophora* | | | |
| Stable Fly: | 4.77 | N.D. | 50 |
| *Stomoxys calcitrans* | | | |
| House fly: | 4.77 | N.D. | 85 |
| *Musca domestica* | | | |
| Cat flea: | 0.477 | N.D. | 50 |
| *Ctenocephalides felis* | | | |

TABLE 1-continued

Effect of Oostatic Hormone on Egg Development and Trypsinlike Enzymes Biosynthesis in Several Species of Insects.

| Insect Species | Oostatic hormone (nmol) | Inhibition of ovarian development (%) | Inhibition of trypsin synthesis (%) |
|---|---|---|---|
| (bouche) | | | |

Female insects were injected with 0.5 μl to 1.0 μl hormone solution of analog 1 or saline and analyzed 24 hours later for egg development.
N.D. = not determined.
No inhibition of egg development of proteolytic enzymes were found in controls injected with saline, or water.

The insects were evaluated for the effect of oostatic hormone 24 hours after injecting the hormone by dissecting out the ovaries and measuring the yolk in each follicle, or by dissecting out the midgut and determining trypsin biosynthesis as was described by Borovsky, D. (1988), Arch. Insect Biochem. Physiol. 8:249-260. We believe that we have discovered an effective method that can interfere with the biosynthesis of serine esterases (trypsinlike or chymotrypsinlike enzymes) in the midgut of insects.

The peptides appear to be less active or completely inactive against insects that do not synthesize trypsinlike enzymes to digest their food. These insects are usually non-blood sucking insects, and may synthesize other digestive enzymes in their gut. Specifically tested were the stored product insects, almond moth and hide beetle that utilize other digestive processes like enzymes against amylases and thus do not depend solely on the synthesis of trypsinlike enzymes in their gut. In insects that egg development is asynchronous, e.g. house flies and dog flies egg development measurements are difficult and were not used. In mosquitoes, on the other hand, synchronous egg development can easily be correlated with the inhibition of protease biosynthesis. Synchronous egg development means that "all or none" of the eggs will be developed.

We expect that treatment of pest insects such as flies or cockroaches would tend to be localized in a small area rather than widely dispersed like treatment of mosquitoes. We expect no effect upon fish or fowl or other insects if the peptides are ingested directly. Also, no effect is expected upon consumption of treated insects or affected insects. The oostatic hormone peptides do not have an effect when inside the gut or other parts of the digestive system (Borovsky, D. [1988] Arch. Insect Biochem. Physiol. 7:187-210). The material must enter and be present in the blood (hemolymph) of an insect to be effective.

These peptides are highly stable in water solution at different pHs (5-9). Peptide (1) was allowed to stand at room temperature in solution of mosquito homogenate (including their digestive enzymes) for two weeks without loss of activity. The structure of these peptides render them undigestible with known endopeptidases (i.e. proteolytic enzymes like trypsin, pronase, etc.). The peptides were not affected by 1% trifluoroacetic acid and were routinely purified using this acid on HPLC. DNA sequences encoding the peptides of the invention can be used as probes to locate the genes expressing these peptides.

DETAILED DESCRIPTION OF THE INVENTION

The one-letter symbol for the amino acids used herein is well known in the art. For convenience, the relationship of the three-letter abbreviation and the one-letter symbol for amino acids is as follows:

| | |
|---|---|
| Ala | A |
| Arg | R |
| Asn | N |
| Asp | D |
| Cys | C |
| Gln | Q |
| Glu | E |
| Gly | G |
| His | H |
| Ile | I |
| Leu | L |
| Lys | K |
| Met | M |
| Phe | F |
| Pro | P |
| Ser | S |
| Thr | T |
| Trp | W |
| Tyr | Y |
| Val | V |

The novel peptides of the invention can be prepared by well-known synthetic procedures. For example, the peptides can be prepared by the well-known Merrifield solid support method. See Merrifield (1963), J. Amer. Chem. Soc. 85:2149-2154 and Merrifield (1965), Science 150:178-185. This procedure, though using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulation since removal of the excess reagents at each step is effected simply by washing of the polymer.

Alternatively, these peptides can be prepared by use of well-known molecular biology procedures. The genes encoding the peptides of the invention can be synthesized readily because the amino acid sequences are disclosed herein. These genes can be used to genetically engineer bacteria, baculovirus, or fungi for synthesis of the peptides of the invention.

The insect cell line Sf9 (*Spodoptera frugiperda*), deposit number ATCC CRL 1711, is available from the American Type Culture Collection, 12301 Parklawn Drive, Rockville, Md. 20852 USA. Baculovirus *Autographa californica* nuclear polyhedrosis virus (AcNPV) is available from Texas A & M University, Texas Agricultural Experiment Station, College Station, Tex. 77843, and has been described in Smith, G. and Summers, M. D. (1978) Virology 89:517-527; and (1979) J. Virology 30:828-838.

Other nuclear polyhedrosis viruses (See World Health Organization Technical Report No. 531) such as *Spodoptera frugiperda* (Sf MNPV), *Choristoneura fumiferana* (Cf MNPV) (Smith, G. and Summers, M. D. [1981] J. Virol. 39 125-137), or *Spodoptera littoralis* (Sl NPV) (Harrap, K. A., Payne, C. C. and Robertson, J. S. [1977] Virology 79:14-31) can be used instead of *Autographa californica* NPV. Other insect cell lines can also be substituted for *Spodoptera frugiperda* (Sf9), for example, *Trichoplusia ni* (Volkman, L. E. and Summers, M. D. [1975] J. Virol. 16:1630-1637), *Spodoptera exigua*, *Choristoneura fumiferana* (Smith, G. and Summers, M. D. [1981] J. Virol. 39:125-137) and *Spodoptera littoralis* (Harrap, K. A. et al. [1977] Virology 79:14-31).

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restrictions enzyme digestions, electrophorese DNA fragments, tail and anneal plasmid and insert DNA, ligate DNA, transform cells, e.g., *E. coli* cells, prepare plasmid DNA, electrophorese proteins, and sequence DNA.

More specifically a wide variety of ways are available for introducing the genes expressing the peptides into the microorganism host under conditions which allow for stable maintenance and expression of the gene. One can provide for DNA constructs which include the transcriptional and translational regulatory signals for expression of the peptide gene.

The transcription initiation signals will include a promoter and a transcriptional initiation start site. In some instances, it may be desirable to provide for regulative expression of the peptide, where expression of the peptide will occur only after release into the environment of the insect. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of the peptide, but upon the release into the environment, expression would begin. Other techniques may employ a specific nutrient medium in the laboratory, which inhibits the expression of the peptide, where the nutrient medium in the environment would allow for expression of the peptide. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a termination region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence, as a double strand may be used by itself for transformation of a microorganism host, but will usually be included with a DNA sequence involving a marker, where the second DNA sequence may be joined to the peptide expression construct or may be combined as a separate DNA fragment with the peptide expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototrophy to an auxotrophic host, or the like. Preferably, complimentation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the peptide. In this manner, the enhanced expression of a siderophore may provide for a competitive advantage for the peptide producing host, so that it may effectively compete with the wild-type microorganisms and stably occupy a niche in the environment of the blood-ingesting insect.

Where no functional replication system is present, the construct will also include a sequence of at least 50 bp, preferably at least about 100 bp of a sequence homologous with a sequence in the host. In this way, the probability of legitimate recombination is enhanced, so that the gene will be integrated into the host and stably maintained by the host. Desirably, the peptide gene will be in close proximity to the gene providing for complementation as well as the gene providing for the competitive advantage. Therefore, in the event that the peptide gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, the lambda left and right promoters, the Tac promoter, the naturally-occurring promoters associated with the peptide gene, where functional in the host. See for example, U.S. Pat. Nos. 4,332,898; 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069 and Bagdasarian et al., (1981) Gene 16:237, and U.S. Pat. Nos. 4,356,270; 4,362,817 and 4,371,625.

In applications to the environment of the blood-ingesting insect the transformant strain will be applied to the natural habitat of the insect. The transformant strain will grow in the insect upon ingestion, while producing the peptide(s) which will have a deleterious effect on proteolytic enzymes biosynthesis and the ova. The organism may be applied by spraying, soaking, injection into the soil, seed coating, seedling coating or spraying, or the like. Where administered in the field, generally concentrations of the organism will be from $10^6$ to $10^{10}$ cells/ml, and the volume applied per hectare will be generally from about 0.1 oz to 2 lbs or more. Where administered to a plant part inhabited by the target insect, the concentration of the organism will usually be from $10^3$ to $10^6$ cells/cm$^2$.

In aquatic environments, insect control may be attained below the surface by varying the lipid content of the transformant microorganism strain. It is known that indigenous aquatic algae float due to their lipid content. A variation in lipid content will allow the transformant strain to be distributed at desired depths below the water surface.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^5$ to $10^9$ cells/ml and may then be employed for introduction into the environment of the blood-ingesting insect.

Following are examples which illustrate procedures, including the best mode, for practicing the invention. These examples should not be construed as limiting. All percentages are by weight and all solvent mixture proportions are by volume unless otherwise noted.

EXAMPLE 1

Treating Mosquitos With Peptides of the Invention (a) Female *Aedes aegypti* were fed blood on a chicken, lightly anesthetized with ether, and immediately injected with different concentrations (1 to 5 μg; 0.25 to 0.5 μl) of synthetic analogs of oostatic hormone (1 and 2). Oostatic hormone analogs are not toxic, as evidenced by the fact that none of the injected mosquitoes died. Twenty-four hours after the injection of oostatic hormone analogs, or water as a control, egg development and trypsinlike enzyme biosynthesis was determined (Borovsky, D. (1988), Arch, Ins. Biochem. Physiol. 7:187–210). (See Table 2)

Egg development in female *Aedes aegypti* was proportional to the dose injected (Table 2). For example, at 2.33 nmol a 98% inhibition of egg development was observed with analog (1), whereas injecting 1.15 nmol of analog (1) reduced the inhibition to 76% (Table 2). The amount of trypsin synthesized in the gut was also reduced (Borovsky, D. [1988], Arch. Ins. Biochem. Physiol. 7:187–210). A four-fold reduction in trypsinlike enzyme content was found compared with controls. Both analogs (1) and (2) had the same effect as injection of natural, purified oostatic hormone (Borovsky, D. (1985), Arch, Ins. Biochem. Physiol. 2:333–349 and Borovsky, D. [1988], Arch. Ins. Biochem. Physiol. 7:187–210).

(b) Another procedure was to dissolve oostatic hormone analogs (1) or (2) in a solvent that might facilitate transport through the cuticular barrier into hemolymph. Dimethylsulfoxide was used and 10 to 20 μg of (1) or (2) was applied topically to houseflies and stableflies in 1 to 10 μl of DMSO. Some evidence of activity in treated insects 24 hours after treatment was manifested that could be classified as sterilization through inhibition of trypsin-like enzyme synthesis.

TABLE 2

Inhibition of Egg Development in *Aedes aegypti* with Synthetic Analogs of Oostatic Hormone.

| Oostatic hormone analog | Number of females (n) | Amount injected (μg) | Amount injected (nmol) | Yolk length (μm) | Inhibition (%) |
|---|---|---|---|---|---|
| 1 | 17 | 2.44 | 2.33 | 53 ± 3 | 98 |
| 1 | 18 | 1.20 | 1.15 | 82 ± 3 | 76 |
| 2 | 9 | 1.92 | 1.83 | 55 ± 11 | 96 |
| 2 | 13 | 0.96 | 0.92 | 102 ± 11 | 62 |
| 1 + 2[a] | 19 | 2.16 | 2.06 | 46 ± 5 | 100 |
| 1 + 2[b] | 16 | 1.04 | 0.99 | 83 ± 9 | 76 |
| Control | 7 | 0 | 0 | 186 ± 6 | 0 |

Groups of female *Aedes aegypti* were injected with 0.5 to 0.25 μl of oostatic hormone analogs, or with 0.5 μl of water as control.
[a]Consist of 1.2 μg (1) and 0.96 μg (2).
[b]Consist of 0.56 μg (1) and 0.48 μg (2).

We claim:

1. An isolated DNA molecule encoding a peptide selected from the group consisting of $H_2N$-YDPAPPPPP-COOH; $H_2N$-DYPAPPPPP-COOH; and $H_2N$-PAPPPPP-COOH.

2. The DNA molecule of claim 1 encoding $H_2N$-YDPAPPPPP-COOH.

3. The DNA molecule of claim 1 encoding $H_2N$-DYPAPPPPP-COOH.

4. The DNA molecule of claim 1 encoding $H_2N$-PAPPPPP-COOH.

5. A procaryotic vector or baculovirus vector comprising heterologous DNA encoding a peptide selected from the group consisting of $H_2N$-YDPAPPPPP-COOH; $H_2N$-DYPAPPPPP-COOH; and $H_2N$-PAPPPPP-COOH.

6. The vector of claim 5 wherein said peptide has the formula $H_2N$-YDPAPPPPP-COOH.

7. The vector of claim 5 wherein said peptide has the formula $H_2N$-DYPAPPPPP-COOH.

8. The vector of claim 5 wherein said peptide has the formula $H_2N$-PAPPPPP-COOH.

* * * * *

UNITED STATES PATENT AND TRADEMARK OFFICE
CERTIFICATE OF CORRECTION

PATENT NO. : 5,130,253

DATED : July 14, 1992

INVENTOR(S) : Dov Borovsky, David A. Carlson

It is certified that error appears in the above-identified patent and that said Letters Patent is hereby corrected as shown below:

Column 2: line 7: "caroxyl" should read --carboxyl--; line 22: "may possible" should read --may be possible--.

Signed and Sealed this

Twenty-eighth Day of September, 1993

*Attest:*

BRUCE LEHMAN

*Attesting Officer*   Commissioner of Patents and Trademarks